United States Patent [19]

Almgren et al.

[11] Patent Number: 5,155,133

[45] Date of Patent: Oct. 13, 1992

[54] ANTIARRHYTHMIC COMPOUNDS AND PHARMACEUTICAL COMPOSITIONS AND METHODS THEREOF

[75] Inventors: Olle K. S. Almgren, Göteborg; Göran B. D. Duker, V. Frölunda; Gert C. Strandlund, Mölndal, all of Sweden

[73] Assignee: Aktiebolaget Hassle, Sweden

[21] Appl. No.: 643,161

[22] Filed: Jan. 18, 1991

Related U.S. Application Data

[63] Continuation of Ser. No. 289,629, Dec. 22, 1988, abandoned.

[30] Foreign Application Priority Data

Dec. 23, 1987 [SE] Sweden ................................ 8705150

[51] Int. Cl.$^5$ ................... A61K 31/275; C07C 255/50
[52] U.S. Cl. ..................... 514/524; 558/413; 558/422
[58] Field of Search ................ 558/413, 422; 514/523, 514/524

[56] References Cited

U.S. PATENT DOCUMENTS 4,544,654 10/1985 Davey et al. .................. 544/58.1

FOREIGN PATENT DOCUMENTS

| 0245997 | 11/1987 | European Pat. Off. |
| 1593771 | 4/1967 | Fed. Rep. of Germany |
| 2503222 | 7/1976 | Fed. Rep. of Germany |
| 0404793 | 10/1978 | Sweden |
| 421123 | 11/1981 | Sweden |
| 1069345 | 5/1967 | United Kingdom |
| 1433920 | 4/1976 | United Kingdom |
| 1457876 | 12/1976 | United Kingdom |

OTHER PUBLICATIONS

G. Duker, et al., Pharmacology & Toxicology, 1988, 63, 85–90.
O. Arunlakshana, et al., Brit. J. Pharmacol. (1959), 14, 48.
Jan E. Alenborg, Computer Methods and Programs in Biomedicine, 28 (1989) 75–85.
Jen T. Weng, M.D., et al., Antiarrhythmic Drugs: Electrophysiological Basis of Their Clinical Use, Am. Thorac. Surg. 1986, 41, 106–112, Williams Foye, Principles of Medicinal Chemistry, 2nd Ed. (1981) pp. 384–385.
Edward Carmeliet, J. Mol. Cell. Cardiol., 23 (Supplement V) (1991) S.79.
Supplement to Circulation, vol. 80 No. 4, Oct. 1989, Abst. No. 2411, 2412.

Primary Examiner—Joseph Paul Brust
Assistant Examiner—Jacqueline Haley
Attorney, Agent, or Firm—White & Case

[57] ABSTRACT

A compound of the formula

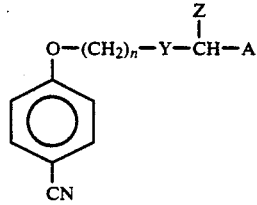

and when appropriate in the form of a racemic mixture or in the form of a stereoisomeric component and the pharmaceutically acceptable salts thereof, in which formula n is an integer 0, 1 or 2
Y is $[CH_2]_m$, CHOH, $CHOCH_3$, CHNHR or CHF,
 m is an integer 0 or 1 and
 R is hydrogen, methyl or ethyl,
Z is hydrogen or a saturated or unsaturated, straight or branched alkyl group containing 1–3 carbon atoms,
A is a group

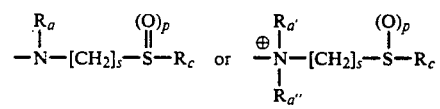

wherein $R_a$ is a straight or branched hydroxyalkyl or an alkyl group containing 1–5 carbon atoms and optionally substituted by one or more fluoro atoms,
 $R_c$ is a saturated or unsaturated, straight or branched alkyl group containing 1–4 carbon atoms and optionally substituted by one or more fluoro atoms,
 $R_{a'}$ is the same as Ra and independently of $R_{a''}$,
 $R_{a''}$ is the same as Ra and independently of $R_{a'}$,
 p is an integer 0, 1 or 2,
 s is an integer 2, 3, 4, 5 useful for the treatment of cardiac arrhythmia, pharmaceutical compositions containing such compounds as active ingredients, processes for preparation of such compounds as well as intermediates for their preparation.

22 Claims, No Drawings

ANTIARRHYTHMIC COMPOUNDS AND PHARMACEUTICAL COMPOSITIONS AND METHODS THEREOF

This application is a continuation of application Ser. No. 289,629, filed on Dec. 22, 1988 abandoned.

DESCRIPTION

1. Field of the Invention

The present invention relates to novel, pharmacologically active compounds and to processes for their preparation. The invention also relates to pharmaceutical compositions containing the compounds and to methods of their pharmacological use.

The object of the invention is to provide substances useful in the treatment, acute as well as long term, of cardiac arrhythmias of diverse etiology.

2. Background Art

GB 1 433 920 discloses compounds of the formula

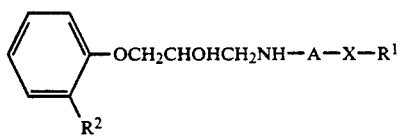

wherein $R^1$ for instance stands for an alkyl or cycloalkyl radical or an aryl radical, $R^2$ for instance stands for halogen, CN or $NO_2$ radical, A stands for an alkylene radical of from 2 to 6 carbon atoms and X stands for —S—, —SO— or —$SO_2$— radical.

These compounds are said to possess $\beta$-adrenergic blocking activity.

GB 1 457 876 discloses among others the compounds

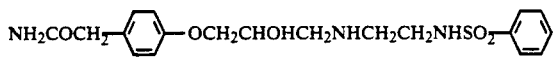

and

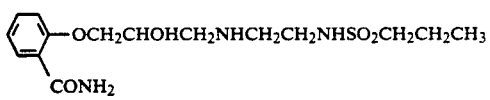

These compounds are said to possess $\beta$-adrenergic blocking activity.

DISCLOSURE OF THE INVENTION

The present invention concerns new compounds useful for treatment, acute as well as long term, of cardiac arrhythmics of diverse etiology.

An object is to provide antiarrhythmics which have less prominent side effects than existing antiarrhythmic drugs. The compounds should for instance be free of negative inotropic effect and the compounds may even be positively inotropic. The compounds should further separate the antiarrhythmic effect from central nervous and gastrointestinal effects.

The compounds of the invention are characterized by the general formula

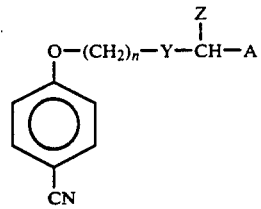

I and when appropriate in the form of a racemic mixture or in the form of a stereoisomeric component and the pharmaceutically acceptable salts thereof, in which formula n is an integer 0,1 or 2

Y is $[CH_2]_m$, CHOH, $CHOCH_3$, CHNHR or CHF, m is an integer 0 or 1 and

R is hydrogen, methyl or ethyl,

Z is hydrogen or a saturated or unsaturated, straight or branched alkyl group containing 1-3 carbon atoms, A is a group

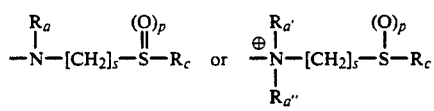

wherein $R_a$ is a straight or branched hydroxyalkyl or alkyl group containing 1-5 carbon atoms and optionally substituted by one or more fluoro atoms, $R_c$ is a saturated or unsaturated, straight or branched alkyl group containing 1-4 carbon atoms and optionally substituted by one or more fluoro atoms, $R_a'$ is the same as $R_a$ and independently of $R_a''$ $R_a''$ is the same as $R_a''$ and independently of $R_a'''$.

p is an integer 0, 1 or 2, s is an integer 2, 3, 4 or 5.

Halogen atoms in formula I comprise fluorine, chlorine, bromine and iodine

Alkyl groups in formula I which are straight and saturated are for instance methyl, ethyl, n-propyl, n-butyl.

Alkyl groups in formula I which are straight and unsaturated are for instance vinyl, allyl, propenyl, —C≡CH, —$CH_2$—C≡CH and —C≡$CCH_3$.

Alkyl groups in formula I which are branched and saturated are for instance i-propyl, s-butyl, i-butyl, t-butyl.

Alkyl groups in formula I which are branched and unsaturated are for instance

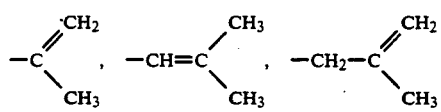

Alkyl groups in formula I which are substituted by fluorine are for instance 1-3 H changed for F in the definition for alkyl groups which are straight and saturated or branched and saturated for instance $CH_2CHFCH_3$, $CH_2CH_2CF_3$, $CH_2CF_2CH_3$, etc.

Alkyl groups in formula I which are substituted by hydroxy are for instance $CH_2-OH$, $CH_2-CH_2-OH$, $\underset{|}{CH}-CH_3$,
$\overset{OH}{\underset{|}{CH}}-CH_2-CH_3$, $CH_2-\overset{OH}{\underset{|}{CH}}-CH_3$, $CH_2-CH_2-\overset{OH}{\underset{|}{CH_2}}$ $\overset{OH}{\underset{|}{CH}}-CH_2-CH_2-CH_3$, $CH_2-\overset{OH}{\underset{|}{CH}}-CH_2-CH_3$, $CH_2-CH_2-\overset{OH}{\underset{|}{CH}}-CH_3$, $CH_2-CH_2-CH_2-OH$.

Preferred groups of compounds of the invention are obtained when n is 1
Y is CHOH, CHF or $(CH_2)_m$
wherein m=1
Z is hydrogen $$A \text{ is } \overset{R_a}{\underset{|}{N}}-(CH_2)_s-\overset{(O)_p}{\underset{||}{S}}-R_c, \text{ where}$$

$R_a$ is $CH_3$, $C_2H_5$, $C_3H_7$, $CH_2CH_2OH$, $CH_2CHOHCH_3$, $R_c$ is $C_2H_5$, $C_3H_7$, $CH_2CHFCH_3$, s is 3, 4, p is 0, 1, 2.

Especially preferred compounds are the sulfoxides i.e. when p is 1.

The following compounds of this group are especially preferred, compounds wherein Y is CHOH or $(CH_2)_m$, $R_a$ is $C_2H_5$, $CH_2CH_2OH$, s is 3, p is 1, $R_c$ is $C_3H_7$.

A preferred compound can also be a quarternary nitrogen compound, obtained from the preferred compounds above by alkylation at the amino group.

Preferred compounds are
4-[3-[ethyl[3-(propylthio)propyl]-amino]-2-hydroxypropoxy]benzonitrile,
4-[3-[ethyl[3-(propylsulfinyl) propyl]amino]-2-hydroxypropoxy]-benzonitrile,
4-[3-[ethyl[3-(propylsulfonyl)propyl]amino]-2-hydroxypropoxy]-benzonitrile
4-[3-[ethyl[3-(methylsulfinyl) propyl]amino]-2-hydroxypropoxy]-benzonitrile
3-[(4-cyanophenoxy)-N,N-diethyl-2-hydroxy-N-[3-(propyl-sulfinyl)propyl]-1-propanaminium iodide
4-[3-[ethyl[3-(propylthio)propyl]amino]-2(R)-hydroxypropoxy]-benzonitrile
4-[3-[ethyl[3-propylsulfinyl)propyl]amino]-2(R)-hydroxy-propoxy]-benzonitrile
4-[3-[ethyl[3-(propylthio)propyl]amino]-2(S)-hydroxypropoxy]benzonitrile
4-[3-[ethyl[3-(propylsulfinyl)propyl]amino]-2(S)-hydroxypropoxy]-benzonitrile
4-[3-[ethyl[4-(ethylthio)butyl]amino]-2-hydroxypropoxy]benzonitrile
4-[3-[ethyl[4-(ethylsulfinyl)butyl]amino]-2-hydroxypropoxy]benzonitrile
4-[3-[2-hydroxyethyl)[3-(propylthio)propyl]amino]-propoxy]benzonitrile
4-[3-[(2-hydroxyethyl)[3-(propylsulfinyl)propyl]amino]propoxy]-benzonitrile
4-[3-[(2-hydroxyethyl)[3-(propylsulfonyl)propyl]amino]propoxy]-benzonitrile
4-[3-[(2-hydroxyethyl)[3-(methylthio)propyl]amino]-propoxy]-benzonitrile
4-[3-[(2-hydroxyethyl)[3-(methylsulfinyl)propyl]amino]propoxy]-benzonitrile
4-3-[ethyl[3-(propylsulfinyl)propyl]amino]-2-hydroxypropoxy]-benzonitrile, addition salt with hydrochloric acid
4-[3-[ethyl[3-(propylsulfinyl)propyl]amino]-2-hydroxypropoxy]-benzonitrile, addition salt with biphenyl-2,2'-diyl hydrogen phosphate
4-[3-[methyl[3-(2-propenyl-1-thio)propyl]amino]-2-hydroxypropoxy]-benzonitrile
4-[3-[ethyl[3-(2-fluropropyl)thio propyl]amino]-2-hydroxypropoxy]-benzonitrile
4-[3-[ethyl[3-[(2-fluoropropyl)sulfinyl)propyl]amino]-2-hydroxypropoxy]-benzonitrile
4-[3-[ethyl[3-(propylsulfinyl)propyl]amino]-2-fluoropropoxy -benzonitrile
More preferred compounds are
4-[3-[ethyl[3-(propylthio)propyl]amino]-2-hydroxypropoxy]benzonitrile,
4-[3-[ethyl[3-(propylsulfinyl) propyl]amino]-2-hydroxypropoxy]-benzonitrile,
4-[3-[ethyl[3-(propylsulfonyl)propyl]amino]-2-hydroxypropoxy]-benzonitrile
3- (4-cyanophenoxy)-N,N-diethyl-2-hydroxy-N-[3-(propyl-sulfinyl)propy]-1-propanaminium iodide
4-[3-[ethyl[3-(propylthio)propyl]amino]-2(R)-hydroxypropoxy]-benzonitrile
4-[3-[ethyl[3-(propylsulfinyl)propyl]amino]-2(R)-hydroxy-propoxy]-benzonitrile
4-[3-[ethyl[3-(propylthio)propyl]amino]-2(S)- hydroxypropoxy]benzonitrile
4-[3-[ethyl[3-(propylsulfinyl)propyl]amino]-2(S)-hydroxypropoxy]-benzonitrile
4-[3-[ethyl[4-(ethylthio)butyl]amino]-2-hydroxypropoxy]benzonitrile
4-[3-[ethyl[4-(ethylsulfinyl)butyl]amino]-2-hyroxypropoxy]benzonitrile
4-[3-[(2-hydroxyethyl)[3-(propylthio)propyl]amino]-propoxy]benzonitrile
4-[3-[(2-hydroxyethyl)[3-(propylsulfinyl)propyl]amino]propoxy]-benzonitrile
4-[3-[(2-hydroxyethyl)[3-(propylsulfonyl)propyl]amino]propoxy]-benzonitrile
4-[3-[ethyl[3-[(2-fluoropropyl)thio]propyl]amino]-2-hydroxypropoxy]-benzonitrile
4-[3-[ethyl[3-[(2-fluoropropyl)sulfinyl)propyl]amino]-2-hydroxypropoxy]-benzonitrile
4-[3-[ethyl[3-(propylsulfinyl)propyl]amino]-2-fluoropropoxy]-benzonitrile
The most preferred compounds are
4-[3-[ethyl[3-(propylsulfinyl) propyl]amino]-2-hydroxypropoxy]-benzonitrile,
4-[3-[ethyl[3-(propylsulfinyl)propyl]amino]-2(R)-hydroxy-propoxy]-benzonitrile
4-[3-[ethyl[3-(propylsulfinyl)propyl]amino]-2(S)-hydroxypropoxy]-benzonitrile
4-[3-[ethyl[4-(ethylsulfinyl)butyl]amino]-2-hydroxypropoxy]benzonitrile
4-[3-[(2-hydroxyethyl)[3-(propylsulfinyl)propyl]amino]propoxy]-benzonitrile 4-[3-[ethyl[3-[(2-fluropropyl)sulfinyl]]propyl]amino]-2-hydroxypropoxy]-benzonitrile 4-[3-[ethyl[3-(propylsulfinyl)propyl]amino]-2-fluoro-propoxy]-benzonitrile Particularly preferred compounds are 4-[3-[ethyl[3-(propylsulfinyl) propyl]amino]-2-hydroxypropoxy]-benzonitrile 4-[3-[ethyl[3-(propylsulfinyl)propyl]amino]-2(R)-hydroxy-propoxy]-benzonitrile 4-[3-[ethyl[3-(propylsulfinyl)propyl]amino]-2(S)-hydroxypropoxy]-benzonitrile 4-[3-[(2-hydroxyethyl)[3-(propylsulfinyl)propyl]amino]propoxy]-benzonitrile In many instances the compounds of formula I occur in stereoisomeric forms, such forms being due to for instance optical isomerism, geometric isomerism and conformations of molecules.

The tertiary amines of the invention can be quarternarized with a lower alkyl group and the quarternary compounds have the same effect as the tertiary compounds.

The new compounds of this invention may be used therapeutically as a stereochemical mixture or in the stereochemical pure forms.

PHARMACEUTICAL PREPARATIONS

In clinical practice the compounds of the present invention will normally be administered orally, rectally or by injection in the form of pharmaceutical preparations comprising the active ingredient either as a free base or as a pharmaceutically acceptable non-toxic, acid addition salt, e.g. the hydrobromide, hydrochloride, phosphate, sulphate, sulphonate, sulphamate, citrate, lactate, maleate, tartrate, acetate and the like in association with a pharmaceutically acceptable carrier. Accordingly, terms relating to the novel compounds of this invention whether generically or specifically are intended to include both the free amine base and the acid addition salts of the free base, unless the context in which such terms are used, e.g. in the specific examples would be inconsistent with the broad concept.

The carrier may be a solid, semisolid or liquid diluent or capsule. These pharmaceutical preparations constitute a further aspect of this invention. Usually the active substance will constitute between 0.1 and 99% by weight of the preparation, more specifically between 0.5 and 20% by weight for preparations intended for injection and between 2 and 50% by weight for preparations suitable for oral administration.

To produce pharmaceutical preparations containing a compound of the invention in the form of dosage units for oral application, the selected compound may be mixed with a solid pulverulent carrier, e.g. lactose, saccharose, sorbitol, mannitol, starches such as potato starch, corn starch or amylopectin, cellulose derivatives, gelatine or other suitable tablet excipients, and a lubricant such as magnesium stearate, calcium stearate, sodium stearyl fumarate, polyethylene glycol waxes, and the like, and then compressed to form tablets. If coated tablets are required, the cores, prepared as described above, may be sugar coated or film coated by conventional film coating polymers.

Dyestuffs may be added to these coatings in order to readily distinguish between tablets containing different active substances or different amounts of the active compound.

For the preparation of soft gelatine capsules (pearl-shaped closed capsules) consisting of gelatine and for example, glycerol or similar closed capsules, the active substance may be admixed with a vegetable oil. Hard gelatine capsules may contain granulates of the active substance in combination with solid, pulverulent carrier such as lactose, saccharose, sorbitol, mannitol, starches (e.g. potato starch, corn starch or amylopectin), cellulose derivatives or gelatine or other suitable pharmaceutically acceptable constituents.

Dosage units for rectal application can be prepared in the form of suppositories comprising the active substance in admixture with a neutral fatty base, or gelatine rectal capsules comprising the active substance in admixture with vegetable oil or paraffin oil.

Liquid preparations for oral application may be in the form of syrups or suspensions, for example solutions containing from about 0.2 to about 20% by weight of the active substance herein described, the balance being sugar alcohols and water optionally mixed with ethanol, glycerol, or propyleneglycol. Optionally such liquid preparations may contain colouring agents, flavouring agents, saccharine and, as a thickening agent, such as carboxymethylcellulose, hydroxypropylmethylcellulose or the like.

Solutions for parenteral applications by injection can be prepared in an aqueous solution of a water-soluble pharmaceutically acceptable salt of the active substance preferably in a concentration of from about 0.5 to about 10% by weight. These solutions may also contain stabilizing agents and/or buffering agents and may conveniently be provided in various dosage unit ampoules.

Suitable doses for oral administration of the compounds of the invention are 1–300 mg 1 to 4 times a day, preferably 20–80 mg 1 to 4 times a day.

METHODS OF PREPARATION

The compounds of the invention may be obtained by any of the following methods.

A. The compounds of the formula I wherein A is

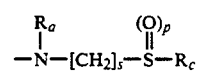

and the symbols n, Y and Z are defined as above, can be obtained by reaction of a compound of the formula

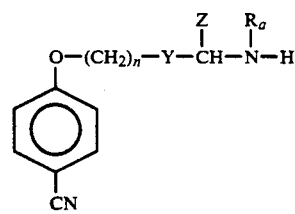

wherein $R_a$ is as defined above with a compound of the formula

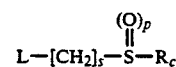

wherein L is a leaving group such as Br, Cl, I, mesyloxy or tosyloxy and s, p and $R_c$ are as defined above.

The reaction is typically carried out in a suitable organic solvent such as acetonitrile, isopropanol or N,N-dimethylformamide. A suitable organic or inorganic base (acid acceptor) such as triethylamine or potassium carbonate is added to the mixture. The mixture is then heated to a temperature in the range of 40°–100° C. until the reaction is completed after which the products can be isolated and purified by conventional methods.

B. The compounds of the formula I wherein p is an integer 1 or 2 can be obtained by oxidation of a compound of the formula I wherein p is an integer 0.

When the substrate is an amine it could be neutralized with a suitable acid, e.g. p-toluene sulfonic acid in a solvent where the salt is soluble e.g. ethanol. When the sulfoxide (p=1) shall be prepared the temperature should be kept between −20°–0° C. When the sulfone (p=2) shall be prepared a temperature in the range 20°–80° C. could be used.

C. The compounds of the formula I wherein n = 1,
Y = CHOH,
Z = H,
p = 1 or 2,
$R_a$, $R_c$ and s have the meaning given above, can be prepared by reaction of a compound of the formula

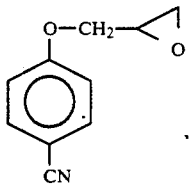

with a compound of the formula

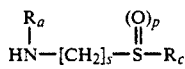

wherein $R_a$, $R_c$, s and p have the meanings given above.

The reaction is typically carries out in a suitable solvent such as isopropanol or N,N-dimethylformamide. The mixture should be heated to a temperature in the range 40°–100° C. until the reaction is completed. Thereafter the product can be isolated by conventional methods.

D. The compounds of the formula I wherein n = 1

Y = CHOH

Z = H p = 0, 1, 2

$R_a$, $R_c$ and s having the meanings above, can be prepared by a reaction of a compound of formula

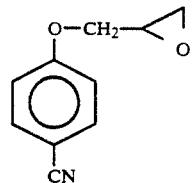
V with a compound of the formula

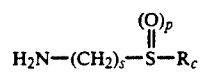

The reaction conditions are the same as described in method C above.

The product from this reaction step, having the formula

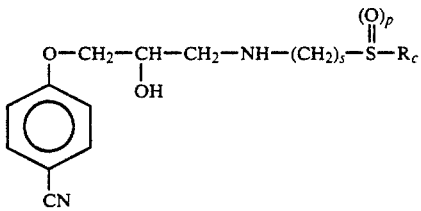

in then alkylated by conventional methods by a suitable alkylating agent of a formula $R_a$-L, where L is a leaving group defined as above, to yield the compound of the formula I as defined above.

When the sulfur atom in the product has a lower oxidation state (e.g. p=0 or 1) it can be further oxidized to products with sulfur atoms of higher oxidation states (e.g. p=1 or 2) described in method B above.

E. A compound of the formula

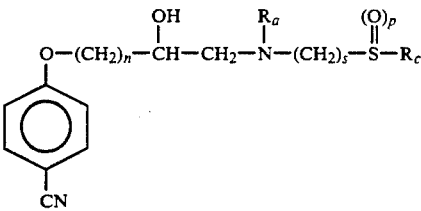

where $R_a$, $R_c$, n, p and s have the meaning above can be prepared by reacting a compound of the formula

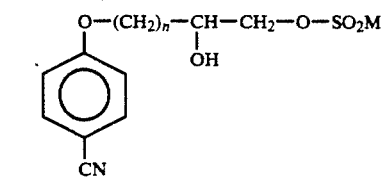

where M is a methyl or a 4-methyl-phenyl residue, with a compound of the formula

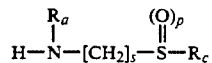
III

The reaction is typically carried out in a suitable organic solvent such as acetonitrile or N,N-dimethylformamide. A suitable organic or inorganic base such as triethylamine or potassiumcarbonate is added to the mixture. The mixture is then heated to a temperature in the range of 90°-100° C. until the reaction is completed after which the products can be isolated and purified by conventional methods.

INTERMEDIATES

The compounds of the formula

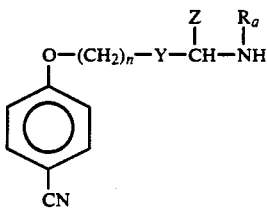
II wherein
n is an integer 0,1 or 2
Y is [CH$_2$]$_m$, CHOH, CHOCH$_3$, CHNHR or CHF,
m is an integer 0 or 1 and
R is hydrogen, methyl or ethyl,
Z is hydrogen or a saturated or unsaturated, straight or branched alkyl group containing 1-3 carbon atoms,
R$_a$ is, a straight or branched hydroxyalkyl or alkyl group containing 1-4 carbon atoms and optionally substituted by one or more fluoro atoms,
are valuable intermediates for the preparation of the compounds of the formula I via the method A. These intermediates are new and constitute a part of the invention.

The compounds of formula II are prepared by reaction of a compound of the formula

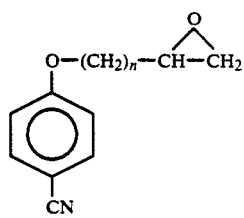

with a compound of the formula R$_a$—NH$_2$
wherein n and R$_a$ have the definitions given above.
Other valuable intermediates are

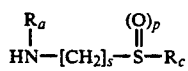
III wherein R$_a$, R$_c$, s and p have the definitions given above. Such intermediates can generally be obtained by a reaction of a compound of the formula

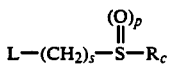

where L is Cl,Br, I, mexyloxy or tosyloxy with an amine of the formula

H$_2$N—R$_a$

A typical procedure in anology with procedure A can be used.
Examples of such intermediates are

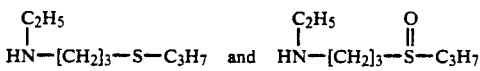

Other valuable intermediates for the preparation of the compounds of the formula I via method D are

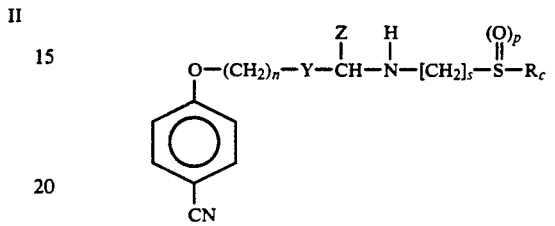

wherein Y, Z, R$_c$, n, s and p have the definitions given above:
Especially valuable are those intermediates wherein s is 3 and p is 0 or 1 such as

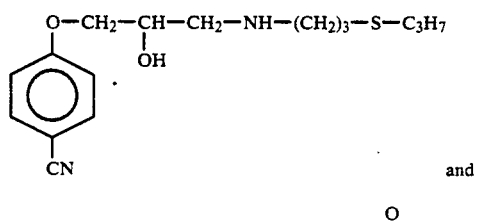

and

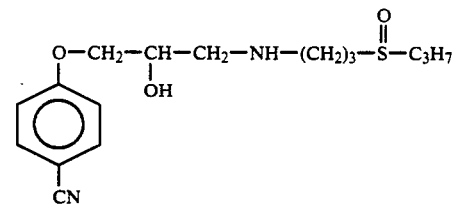

WORKING EXAMPLES

Example 1

4-[3-[ethyl[3-(propylthio)propyl]amino]-2-hydroxy-propoxy]-benzonitrile

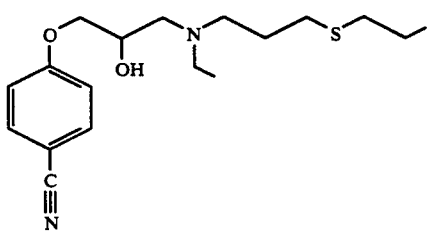

a) 4[-3-(ethylamino)-2-hydroxypropoxy]-benzonitrile 86.0 g of 4-(oxiranylmethoxy) benzonitrile was dissolved in 250 ml acetonitrile and mixed with 29.7 g ethylamine in an autoclave. The mixture was heated in a boiling water-bath over night, evaporated and the residue was dissolved in 2-M hydrochloric acid. This acidic waterlayer was washed twice with ether, alkalized with 10-M sodium hydroxide and extracted with three portions of dichloromethane.

The combined organic layers were dried over sodiumsulfate and evaporated. The solid residue was recrystallized twice from a mixture of diisopropylether: acetonitrile (9:1). Yield 57 g of 4- 3-(ethylamino)-2-hydroxypropoxy -benzonitrile.

NMR: $^{13}$C in CDCl$_3$; 14.88, 43.93, 51.28, 67.60, 70.77, 104.31, 115.26, 119.00, 133.93, 161.93 ppm b) 4-[3-[ethyl[3-(-propylthio) propyl]-amino]-2-hydroxypropoxy]-benzonitrile 4.7 g of 4-[3-(ethylamino)-2-hydroxypropoxy]-benzonitrile, 4.5 g of 1-bromo-3-(propylthio)-propane and 5.8 g potassium carbonate were mixed in 50 ml isopropanol and refluxed over night. The mixture was filtrated and evaporated. The residual oil 8.3 g was separated by column chromatography. Yield 4.9 g of the title compound.

NMR: $^{13}$C in CDCl$_3$; 11.44, 13.47, 22.62, 26.84, 29.56, 34.63, 47.44, 52.27, 56.03, 65.81, 70.47, 103.74, 115.08, 118.78, 133.57, 161.87, ppm Example 2

4-[3-[ethyl[3-(propylsulfinyl)propyl]amino]-2-hydroxypropoxy]-benzonitrile

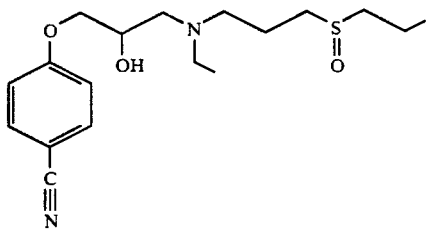

2.45 g of 4-[3-[ethyl[b 3-(propylthio)propyl]amino]-2-hydroxypropoxy]-benzonitrile and 1.4 g p-toluenesulfonic acid were mixed in 50 ml of ethanol. The mixture was cooled to −10° C. and 1.7 g of m-chloroperbenzoic acid was added in small portions. The mixture was stirred for 0.5 hour at −10° C. and one hour at room temperature and then evaporated. The residue was dissolved in dichloromethane and washed with three portions of sodium carbonate and twice with water and thereafter dried over sodium sulfate, filtrated and evaporated. The residue, 2.3 g yellow oil was purified by column chromatography. Yield: 1.4 g of the title compound.

NMR: $^{13}$C in CDCl$_3$; 11.21, 11.33, 13.11, 16.02, 20.30, 20.43, 47.41, 47.45, 49.69, 49.95, 52.18, 52.41, 54.29, 54.41, 56.06, 56.09, 66.08, 70.41, 70.49, 103.76, 115.09, 118.83, 133.62, 161.88 ppm Example 3

4-[3-[ethyl[3-(propylsulfonyl) propyl]amino]-2-hydroxypropoxy]-benzonitrile

4-[3-[ethyl[3-(propylsulfonyl)propyl]amino]-2-hydroxypropoxy]-benzonitrile

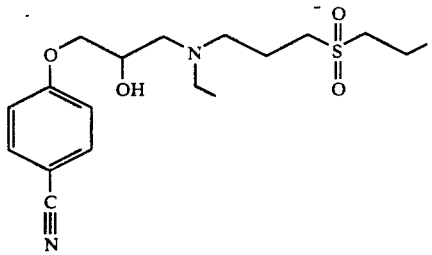

7.3 g of 4-3-[ethyl[3-(propylthio)propyl]amino]-2-hydroxypropoxy]-benzonitrile was mixed with 4.2 g of p-toluenesulfonic acid in 75 ml of ethanol. To this mixture was added 10.1 g of m-chloroperbenzoic acid in small portions. The temperature was allowed to rise to 45° C. during the addition. The mixture was then stirred at room temperature for three hours. After that the reaction was completed, the solvent was evaporated and the residue was dissolved in dichloromethane, washed three times with sodiumcarbonate and twice with water. The organic layer was evaporated and the residue was dissolved in 2-M hydrochloric acid and washed three times with ether. The aqueous layer was made alkaline with 1-M sodium hydroxide solution and extracted with dichloromethane. The organic solutions were dried over sodium sulfate filtrated and evaporated. The crude product 5.4 g was purified by column chromatography. Yield: 3.2 g of the title compound.

NMR: $^{13}$C in CDCl$_3$; 11.41, 12.88, 15.64, 19.57, 47.44, 50.15, 51.88, 54.68, 56.04, 66.19, 70.45, 104.0, 115.2, 118.94, 133.79, 161.91 ppm Example 4

4-[3-[ethyl[3-(methylsulfinyl)propyl]amino]-2-hydroxypropoxy]-benzonitrile

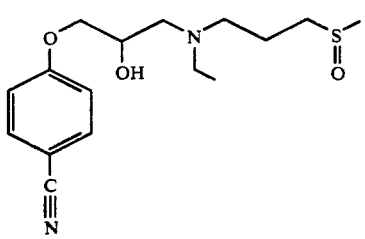

The title compound was prepared in analogy with the methods described in examples 1 and 2.

NMR: $^{13}$C in CDCl$_3$; 11.16, 11.27, 20.18, 20.31, 38.39, 38.50, 47.40, 51.87, 52.11, 52.17, 52.35, 56.02, 66.09, 70.37, 70.44, 103.68, 115.05, 118.79, 133.58, 161.83 ppm Example 5

3-(4-cyanophenoxy)-N,N-diethyl-2-hydroxy-N-[3-(propylsulfinyl)propyl]-1-propanaminium iodide -continued

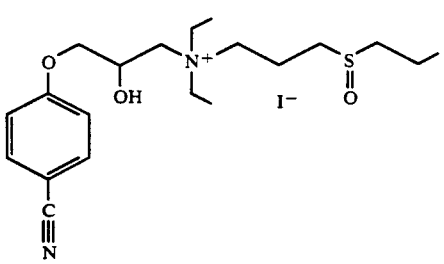

5.0 of 4-[3-[ethyl[3-(propylsulfinyl)propyl]amino]-2-hydroxypropoxy]-benzonitrile and 2.4 g ethyliodide were dissolved in 50 ml of acetronitrile and heated to reflux for 5 hours. Another portion of ethyliodide, 2.4 g, was added and the reflux continued over night. The solution was evaporated and the residual oil, 6.6 g, was separated by column chromatography. Yield: 4.0 g of the title compound.

NMR: $^{13}$C in D$_2$O; 8.07, 13.42, 16.75, 47.73, 53.78, 55.53, 57.57, 60.38, 64.41, 67.42, 70.78, 104.00, 116.45, 120.77, 135.39, 162.35 ppm.

Example 6

4-[3-[ethyl[3-(propylthio)propyl]amino]-2(R)-hydroxypropoxy]benzonitrile

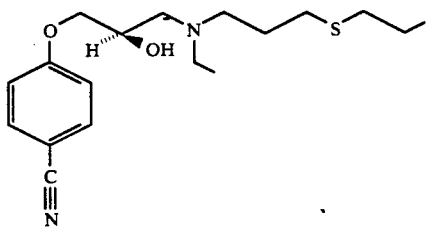

a)
(4S)-2,2-Dimethyl-4-(4-cyanophenoxy)methyl-1,3-dioxolane

A solution of 4-hydroxy benzonitrile (55 g) in methanol (100 ml) was treated with potassium hydroxide (29 g) in water (30 ml) and evaporated at reduced pressure. The remaining potassium salt was dissolved in dry dimethylformamide (75 ml) and (4R)-2,2-dimethyl-4 -methanesulfonyloxymethyl-1,3-dioxolane, 82.2 g, was add stirring at 110° C. for 20 h, allowed to cool and distributed between ether and water. The aqueous phase was extracted three times with ether, the combined ether phases washed three times with 10% aqueous potassium hydroxide and twice with water, dried over anhydrous sodium sulfate and evaporated. Yield 77 g of the title compound.

NMR: $^{13}$C in CDCl$_3$; 25.11, 26.57, 66.35, 68.85, 73.55, 104.30, 109.77, 115.17, 118.83, 133.79, 161.68 ppm.

b) (2R)-3-(4-cyanophenoxy)propane-1,2-diol 77 g of (4S)-2,2-dimethyl-4-(4-cyanophenoxy)methyl-1,3-dioxolane, was dissolved in methanol (200 ml) and water (75 ml). Concentrated hydrochloric acid (0.5 ml) was added and the mixture was kept at 50° C. overnight. It was evaporated at reduced pressure and recrystallized from water to yield 46 g of the title compound as white leaves, m.p. 63°–65° C.

NMR: $^{13}$C in CD$_3$OD; 63.90, 70.72, 71.44, 104.70, 116.56, 120.07, 135.09, 163.86 ppm.

c) (2S)-1-(4-cyanophenoxy)-3-methanesulfonyloxy propan-2-ol 57.2 g of (2R)-3-(4 cyanophenoxy)propane-1,2-diol was dissolved in dry pyridine, (300 ml) and treated dropwise with methanesulfonyl chloride, (20.7 ml), at −10° C. The reaction mixture was kept at 5° C. overnight, evaporated at reduced pressure and poured on ice and 2 M hydrochloric acid. The solid precipitate was recrystallized three times from methanol to yield 12.3 g of the title compound, m.p. 119°–121° C., $[\alpha]_D^{20}$ +9.7° (c 1.0, CH$_3$OH).

NMR: $^{13}$C in CD$_3$OD; 37.26, 68.77, 69.92, 71.76, 105.19, 116.65, 119.99, 35.19, 163.55 ppm.

d)
4-[3-[ethyl[3-(propylthio)propyl]amino]-2(R)-hydroxypropoxy]benzonitrile 11.7 g of (2S)-1-(4-cyanophenoxy)-3-methanesulfonyloxy propane-2-ol, was stirred and refluxed overnight with ethyl (3-propylthio)propylamine (13.9 g), potassium carbonate (12.6 g) and acetonitrile (100 ml). Filtration and evaporation gave 21.5 g of crude product which was distributed between ether and 2 M hydrochloric acid. The aqueous layer was extracted three times with dichloromethane, in which it was present as an ion pair. Evaporation and distribution between ether and 1 M sodium hydroxide yielded the free base in the ether layer. Chromatography over silica using methanol-dichloromethane 5:95 as mobile phase gave 10.3 g of the title compound as a colourless oil, $[\alpha]_D^{20}$ −24,2° (c 1.0, CH$_3$OH).

NMR: $^{13}$C in CDCl$_3$; 11.53, 13.32, 22.76, 26.92, 29.71, 34.20, 47.56, 52.38, 56.20, 65.82, 70.53, 103.97, 115.17, 118.95, 133.98, 161.95 ppm.

Example 7

4-[3-[ethyl[3-(propylsulfinyl)propyl]amino]-2(R)-hydroxypropoxy]benzonitrile

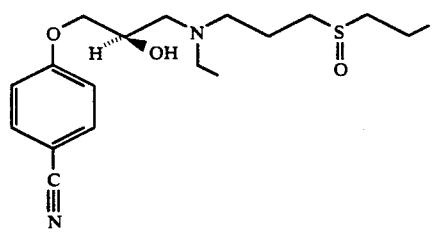

Oxidation of 4-[3-[ethyl[3-(propylthio)propyl]amino]-2(R)-hydroxy propoxy]bensonitrile with m-chloroperbenzoic acid was carried out as described for the racemate in example 2. $[\alpha]_D^{20}$ −18.6° (C 1.0, CH$_3$OH)

NMR: $^{13}$C in CDCl$_3$; 11.35, 11.47, 13.30, 16.24, 20.47, 20.62, 47.59, 47.63, 49.83, 50.12, 52.30, 52.57, 54.53, 54.66, 56.28, 56.31, 66.13, 70.52, 70.60, 104.08, 115.24, 119.02, 133.85, 162.0 ppm.

Example 8

4-[3-[ethyl[3-(propylthio)propyl]amino]-2(S)-hydroxypropoxy]-benzonitrile

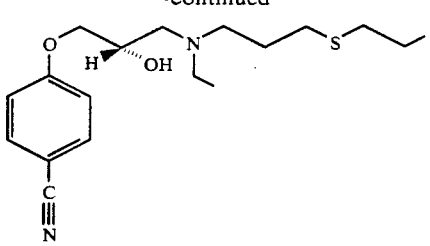

The title compound was prepared in analogy with the method described in example 6. $[\alpha]_D^{20}+24.0°$ (C 1.0, CH$_3$OH).

NMR: $^{13}$C in CDCl$_3$; 11.52, 13.27, 22.74, 26.93, 29.70, 34.19, 47.58, 52.40, 56.22, 65.85, 70.54, 103.96, 115.16, 118.89, 133.72, 161.95 ppm.

Example 9

4-[3-[ethyl[3-(propylsulfinyl)propyl]amino]-2(S)-hydroxypropoxy]-benzonitrile

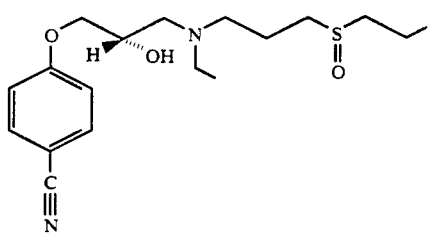

The title compound was prepared in analogy with method described in example 7 and example 2. $[\alpha]_D^{20}+18.0°$ (C 1.0, CH$_3$OH).

NMR: 13C in CDC13; 11.31, 11.43, 13.26, 16.18, 20.41, 20.57, 47.53, 47.58, 49.8, 50.08, 52.26, 52.53, 54.48, 54.61, 56.22, 56.24, 66.09, 70.48, 70.57, 104.0, 115.20, 118.97, 133.79, 161.96 ppm.

Example 10

4-[3-[ethyl[4-(ethylthio)butyl]amino]-2-hydroxypropoxy]benzonitrile

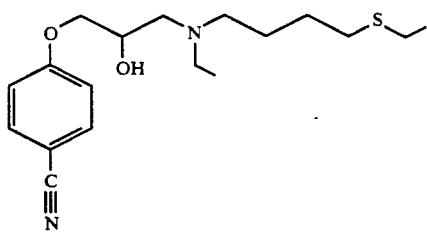

2 g of ethyl-[4 -(ethylthio)butyl]amine and 2.17 g of 4-oxiranylmethoxy)benzonitrile were mixed in 25 ml isopropanol and refluxed over night. The mixture was evaporated and the residual oil was dissolved in 2 M HCl. This acidic waterlayer was washed with three portions of ether and then the HCl-salt of the product was extracted as ion pair with three portions of dichloromethane. The organic layer containing the ion pair was alkalized with 2 M NaOH and the organic layer now containing the base form of the product was dried over sodiumsulfate and evaporated and purified by column chromatography. Yield: 3.7 g of the title compound.

NMR: $^{13}$C in CDCl$_3$; 11.67, 14.65, 25.81, 26.31, 27.18, 31.40, 47.57, 53.16, 56.08, 65.69, 70.64, 104.03, 115.20, 118.97, 133.79, 162.01 ppm.

Example 11

4-[3-[ethyl[4-(ethylsulfinyl)butyl]amino]-2-hydroxypropoxy]benzonitrile

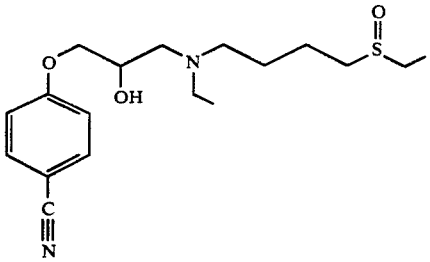

1.68 g of 4-[3-[ethyl[4-(ethylthio)butyl]amino-2-hydroxypropoxy]-benzonitrile was oxidized by 1.1 g of m-chloroperbenzoic acid in analogy with example 2. Yield: 0.7 g of the title compound.

NMR: $^{13}$C in CDCl$_3$; 6.66, 11.52, 20.41, 26.39, 45.67, 47.75, 51.25, 53.12, 56.24, 65.85, 70.54, 115.24, 119.0, 133.84, 104.0, 162.0 ppm.

Example 12

4-[3-[(2-hydroxyethyl)]3-(propylthio)propyl]amino]propoxy]benzonitrile

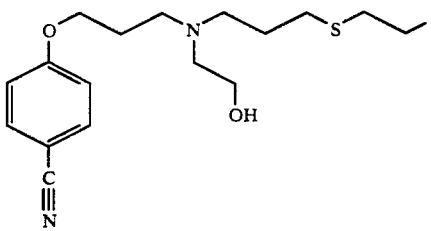

a) 4-[3-[(2-hydroxyethyl)amino]propoxy]benzonitrile

A solution of 3-bromo propoxy benzonitrile (10 g) and ethanolamine (10 g) in 2-propanol (150 ml) was refluxed for 2 hours. After overnight standing, solvent was evaporated. The residue was dissolved in aqueous HCl (2 M) and washed with diethylether. The acidic aqueous layer was basified with sodium hydroxide solution (10 M). Extraction with methylene chloride and evaporation of the solvent gave crude material (7.2 g). Recrystallization from di-isopropylether gave 7.0 g of the title compound with m.p. 88° C.

NMR: $^{13}$C in CDCl$_3$; 29.15, 46.04, 51.09, 60.49, 66.38, 103.55, 115.02, 119.01, 133.74, 162.04 ppm.

b)
4-[3-[(2-hydroxyethyl)[3-(propylthio)propyl]amino]propoxy]benzonitrile

A mixture of 4-[3-[(2-hydroxyethyl)amino]propoxy]benzonitrile (3 g), 1-bromo-3-(propylthio)propane (2.7 g) and potassium carbonate (3.7 g) in 2-propanol (50 ml) was refluxed for 28 hours. The solvent was evaporated and the residue dissolved in aqueous HCl (2 M) and extracted with diethylether. The aqueous layer was basified with sodium hydroxide (10 M) and extracted with methylene chloride followed by drying over sodium sulfate. Evaporation of the solvent gave a crude residue, which was purified by column chromatography. Yield 2.6 g of the title compound as an oil.

NMR: $^{13}$C in CDCl$_3$; 13.13, 22.61, 26.53, 26.73, 29.60, 31.04, 50.11, 52.53, 55.67, 58.66, 66.06, 103.52, 114.92, 118.80, 133.60, 161.92 ppm.

Example 13

4-[3-[(2-hydroxyethyl)[3-(propylsulfinyl)propyl]amino]propoxy]benzonitrile

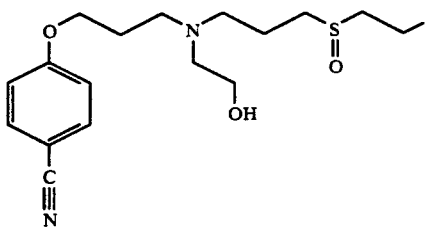

4 g of 4-[3-[(2-hydroxyethyl)[3-(propylthio)propyl]amino]propoxy]-benzonitrile was oxidized with m-chloroperbenzoic acid (2.1 g) in analogy with example 2. The yield, after column chromatography was 2.5 g of the title compound.

NMR: $^{13}$C in CDCl$_3$; 13.37, 16.28, 20.69, 26.66, 50.03, 50.42, 52.92, 54.65, 55.94, 59.09, 66.29, 103.88, 115.21, 119.12, 133.94, 162.18 ppm.

Example 14

4-[3-[(2-hydroxyethyl)[3-(propylsulfonyl)propyl]amino]propoxy]-benzonitrile

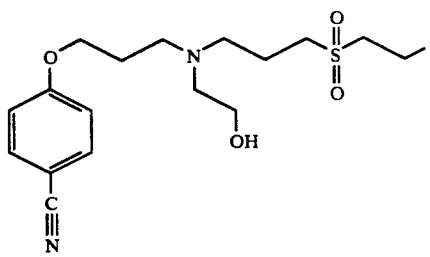

A mixture of 4-[3-[2-hydroxyethyl)amino]propoxy]benzonitrile (1.3 g), 1-bromo-3-(propylsulfonyl)propane (1.3 g) and potassium carbonate (1.6 g) in acetonitrile (100 ml) was refluxed over night. Work up by conventional methods including column chromatography. Yield:0.5 g of the title compound.

NMR: $^{13}$C in CDCl$_3$; 13.00, 15.82, 19.53, 26.51, 50.03, 50.20, 52.18, 54.71, 55.84, 58.98, 66.18, 103.75, 115.11, 119.02, 133.87, 162.01 ppm.

Example 15

4-[3-[(2-hydroxyethyl)[3-(methylthio)propyl]amino]propoxy]-benzonitrile

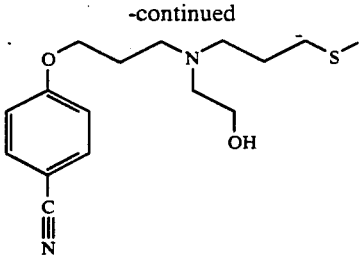

3 g of 4-[3- [2-hydroxyethyl)amin]-propoxy]benzonitrile and 2.2 g 1-bromo-3-(methylthio)propane and 3.7 g of potassium carbonate were mixed in 50 ml isopropanol and refluxed over night. The mixture was filtrated and evaporated, and the residue was dissolved in 2 M hydrochloric acid. This acid water layer was washed twice with ether, alkalized with 10 M sodium hydroxide and extracted with three portions of dichloromethane. The combined organic layers were dried over sodiumsulfate and evaporated. The residual oil was purified by column chromatography. Yield: 1.2 g of the title compound.

NMR: $^{13}$C in CDCl$_3$; 15.60, 26.50, 26.89, 32.13, 50.47, 52.75, 55.99, 58.84, 66.30, 104.06, 115.18, 119.11, 133.98, 162.17 ppm.

Example 16

4-[3-[(2-hydroxyethyl)[3-(methylsulfinyl)propyl]amino]propoxy]-benzonitrile

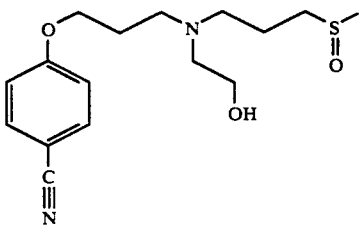

1.1 g of 4-[3-[(2-hydroxyethyl)[3-(methylthio)propyl]amino]propoxy]benzonitrile was oxidized with 0.87 g of m-chloroperbenzoic acid in analogy with example 2. Yield: 0.7 g of the title compound.

NMR: $^{13}$C in CDCl$_3$; 20.42, 26.48, 38.56, 50.28, 52.09, 52.74, 55.75, 58.94, 66.08, 103.67, 115.03, 118.98, 133.77, 161.98 ppm.

Example 17

4-[3-[methyl[3-(2-propenyl-1-thio)propyl]amino-2-hydroxypropoxy]-benzonitrile

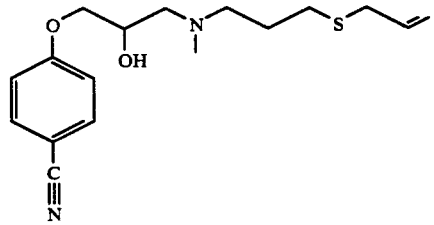

a) 4-[3(methylamino)-2-hydroxypropoxy]-benzonitrile

The title compound was prepared in analogy with the method described in example 1a. mp 100°-102° C.

NMR $^{13}$C in CDCl$_3$; 36.18, 53.82, 67.59, 70.88, 103.97, 115.13, 118.92, 133.79, 161.88.

b) 1-chloro-3(2-propenyl-1-thio)-propane.

A stirred mixture of 2-propene-1-thiol(6.8 g; 92 mmol),1-bromo-3-chloropropane (14.5 g; 92 mmol) and potassiumcarbonate (20 g; 145 mmol) in acetonitrile (50 ml) was warmed at 80° C. for five minutes. Filtration and evaporation gave an oily residue. Vacuum destillation at 10 mm Hg gave a fraction at 65° C. Yield: 7 g (51 %) of an colourless oil.

NMR: $^{13}$C in CDCl$_3$; 27.33, 31.74, 34.45, 43.23, 116,76, 134.03 c)
4-[3-[methyl[3-(2-propenyl-1-thio)propyl]amino]-2-hydroxypropoxy]-benzonitrile A stirred mixture of 4-[3{methylamino)-2-hydroxypropoxy]-benzonitrile (4.12 g; 20 mmol),1-chloro-3(2-propenyl-1-thio)propane (3.5 g; 23 mmol) sodium iodide (3.5 g; 24 mmol) and potassium carbonate (5 g; 36 mmol) in acetonitrile (50 ml) was refluxed for 24 hours. Filtration and evaporation of the solvent gave a residue which was purified by flash chromatography (SiO$_2$; CH$_2$Cl$_2$:CH$_3{IOH}$ (9:1). Yield: 5 g (78 %) of a colourless oil.

NMR: $^{13}$C in CDCL$_3$; 26.62, 28.33, 34.81, 41.97, 56.63, 59.96, 65.82, 70.52, 104.08, 115.22, 116.78, 119.00, 133.84, 134.29, 161.98.

Example 18

4-[3-[ethyl[3-[(2-fluoropropyl)thio]propyl]amino]-2-hydroxypropoxy]-benzonitrile

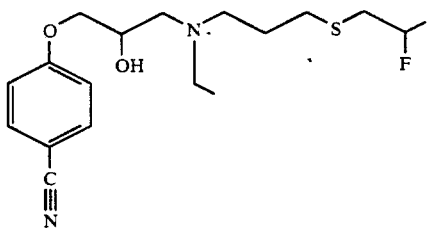

A solution of 1-hydroxy-3-[(2-fluoropropyl)thio]-propane (5.5 g, 36.1 mmol), prepared by conventional methodes from 1-hydroxy-3-thiopropane and 1-bromo-2-fluoropropane, was mixed with triethyl amine(3.9 g, 39.7 mmol) in methylene chloride and was then stirred and cooled to 0° C. Methanesulfonylchloride (4.1 g, 36.1 mmol) was added during a period of 20 minutes. The solution was filtered and washed twice with sodium bicarbonate and water. The yield was 8.2 g. The mesylate was dissolved in acetonitrile (100 ml) and 4-[3-(etylamino)-2-hydroxypropoxy]-benzonitrile (8.7 g, 39.4 mmol) was added. The solution was refluxed over night. The solvent was evaporated and the residue was purified by column chromatography on silica gel. Yield: 5.75 g of the title compound.

NMR: $^{13}$C in CDCL$_3$; 11.46, 19.88, 20.06, 26.87, 30.58, 37.74, 37.92, 47.46, 52.19, 56.07, 65.84, 70.47, 89.52, 90.86, 103.82, 115.11, 118.84, 133.64, 161.90.

Example 19

4-[3-[ethyl[3-[(2-fluoropropyl)sulfinyl]propyl]amino]-2-hydroxypropoxy]benzonitrile

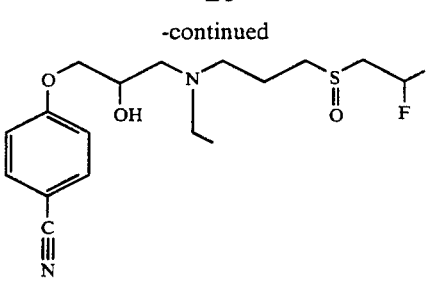

A solution of 4-[3-[ethy[3-[(2-fluoropropyl)thio]-propyl]amino]-2-hydroxypropoxy]-benzonitrile (5,1 g 14.4 mmol) and toluene-4-sulfonic acid (2.73 g, 14.4 mmol) in ethanol (100 ml) was stirred and cooled to −15° C. To the mixture was added a solution of 3-chloroperbenzonic acid (4.5 g, 14.4 mmol)in ethanol (10 ml). The solution was stirred at room temperature for 3 h. Solid calcium hydroxide (2.66 g, 36 mmol) was added and the slurry was stirred for 15 h. The slurry was filtered and evaporated to give an oily residue. The residue was dissolved in 2 M hydrochloric acid and washed with diethylether. The acidic solution was treated with 2 M sodium hydroxide to pH =12 and extracted with methylene chloride. Drying over sodium sulfate and evaporation to dryness gave an oily residue which was purified by column chromatography on silica gel. Yield: 3.2 g of the title compound.

NMR: $^{13}$C in CDCL$_3$; 11.07, 11.09, 11.20, 20.11, 20.25, 20.43, 20.52, 20.62, 20.66, 20.84, 47.44, 47.50, 49.87, 50.11, 50.65, 50.92, 51.32, 52.10, 52.35, 56.12, 56.82, 56.99, 59.39, 59.55, 59.71, 66.08, 70.00, 70.44, 83.48, 83.67, 84.83, 85.01, 103.76, 115.09, 118.84, 136.48, 161.86.

Example 20

4-[3-[ethyl[3-(propylsulfinyl)propyl]amino]-2-fluoropropoxy]-benzonitrile

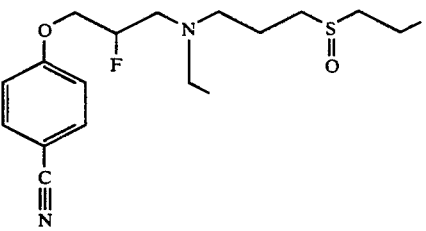

In methylene chloride under argon atmosphere was dissolved (diethylamino)sulfur trifluoride (2.3 g, 14.2 mmol). The solution was cooled to -70° C. To this solution was added dropwise 4-[3-[ethyl -(propylsulfinyl)-propyl]amino]-2-hydroxypropoxy]-benzonitrile (5.0 g, 4.2 mmol) in methylene chloride (5 ml). The solution was stirred at −70° C. for ½ h and at room temperature for 2 h and then treated with water (50 ml) and with sodium hydroxide to pH=11. The resulting layers were separated and the water layer was extracted with methylene chloride. The combined organic fractions were washed with water and dried over sodium sulfate. The oily residue was purified by column chromatography on silica gel. Yield: 1.0 g of the title compound.

NMR: $^{13}$C in CD CL$_3$; 11.69, 13.31, 16.21, 20.45, 20.63, 22.21, 48.31, 49.85, 49.89, 52.96, 53.05, 53.65, 53.69, 53.82, 53.86, 54.49, 54.53, 68.25, 68.28, 68.44, 68.46, 89.63, 89.70, 91.03, 91.10, 104.52, 115.08, 115.25, 118.88, 133.87, 133.94, 161.61.

Example 21

4-[3-[ethyl[3-(propylsulfinyl)propyl]amino]-2-hydroxy-propoxy]benzonitrile, addition salt with hydrochloric acid To a solution of 4-[3-[ethyl[3-(propylsulfinyl)propyl]amino]-2-hydroxy-propoxy]-benzonitrile (1.06 g) in methylene chloride (3 ml) was added a saturated solution of hydrogen chloride in diethylether (3 ml) followed by diethylether (7 ml). Solvent was decanted from the resulting oil, which was washed with diethylether (3×10 ml) and dried under high vacuum. Yield: 1.1 g as an oil.

NMR: $^{13}C$ in $D_2O$, relative dioxane (67.4 ppm); 8.74, 9.17, 13.29, 16.67, 18.23, 18.37, 18.47, 48.01, 49.23, 49.35, 50.97, 51.10, 51.73, 53.32, 53.66, 55.30, 64.77, 64.94, 70.45, 104.01, 116.36, 120.90, 135.36, 162.58 ppm.

Example 22

4-[3-[ethyl[3-(propylsulfinyl)propyl]amino]-2-hydroxypropoxy]benzonitrile, addition salt with biphenyl-2,2'-diyl hydrogen phosphate 4-[3-[ethyl[3-(propylsulfinyl)propyl]amino]-2-hydroxypropoxy]-benzonitrile (0.35 g) and biphenyl-2,2'-diyl-hydrogen phosphate (0.25 g) were dissolved in methylene chloride (2 ml). Addition of diisopropylether (10 ml) gave a colourless precipitate. Solvent was decanted and the solid residue was washed with diethylether. Yield: 0.54 g (90%) of colourless crystals. M.p. 147° C.

NMR: $^{13}C$ in $CDCl_3$; 8.68, 13.25, 16.23, 18.14, 48.38, 48.47, 49.44, 52.50, 54.49, 54.57, 56.14, 64.36, 69.96, 104.63, 115.39, 118.93, 121.64, 124.95, 129.42, 129.71, 133.98, 149.89, 149.96, 161.40 ppm.

Example 23

4-[2-hydroxy-3-[[3(propylthio)propyl]amino propoxy]-benzonitrile

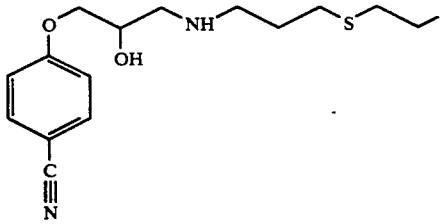

A solution of 4-(oxiranylmetoxy)-benzonitrile (1.32 g, 7.5 mmol) and 3-propylthio-1-propylamine (1 g, 7.5 mmol) in acetonitrile (10 ml) was refluxed over night. The solution was evaporated and the residue was dissolved in 2 M hydrochloric acid. The acidic solution was washed with diethylether, alkalized with 10 M sodium hydroxide and extracted with metylene chloride. The solvent was evaporated and the residue was purified by column chromatography on silica gel. Yield: 1.1 g of the title compound.

NMR: $^{13}C$ in $CDCl_3$: 13.26, 22.67, 29.26, 29.55, 34.09, 48.43, 51.44, 67.61, 70.63, 104.00, 115.15, 118.87, 133.78, 161.82.

Example 24

4-[2-hydroxy-3-[[3(propylsulfinyl)propyl]amino]propoxy]-benzonitrile

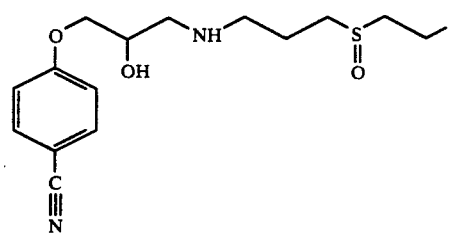

A solution of 4-[2-hydroxy-3-[[3(propylthio)propyl]amino]propoxy]-benzonitrile (0.9 g, 2.91 mmql) and toluene-4-sulfonic acid (0.55 2.91 mmol) in ethanol (20 ml) was stirred and cooled to −15° C. To this solution was added a solution of 3-chloroperbenzoic acid (0.61 g, 2.91 mmol) in ethanol (10 ml) over a period of ten minutes. The mixture was stirred at −10° C. for ½ h and at room temperature for 3 h. Solid calcium hydroxide (0.54 g, 7.27 mmol) was added and the slurry was stirred for ten minutes, filtrated and evaporated. Yield: 0.9 g of the title compound as colourless crystals with mp: 76°-77° C.

NMR: $^{13}C$ in $CDCL_3$; 13.42, 16.34, 23.44, 48.38, 48.15, 50.19, 51.56, 54.69, 68.68, 70.73, 104.32, 115.34, 119.077, 133.99, 162.01.

Example 25

N-ethyl-N[(3-propylthio)propyl]amine

To a solution of 1-propanethiol (228.5 g, 3 mol) and sodium hydroxide (0.2 g) was added acrylonitrile (167.1 g, 3.15 mol) the reaction mixture was stirred over night. Water (100 ml) was added and the organic layer was separated and dried over sodium sulfate. Evaporation gave 398 g of 3-propylthio-propionitrile. A solution of 3-propylthio-propionitrile (194 g, 1.5 mol) in ether(100 ml) was added to a suspension of lithium aluminium hydride (60 g, 1.5 mol) in ether, conventional work up gave 158 g of 3-propylthio-propylamine. All 3-propylthio-propylamine was mixed with acetic anhydride (104 ml, 1.1 mol) and stirred for 1 h. Water (300 ml) was added and extraction with methylene chloride followed by drying over sodium sulfate and evaporation gave 161 g of 3-propylthio-propylacetamide. 3-propylthio-propylacetamide (133 to a suspension of lithium aluminium hydride (42 g, 1.1 mol) in ether. Conventional work up and destillation (100° C./12 mm Hg) yielded 113.8 g of the title compound.

NMR: $^{13}C$ in $CDCL_3$: 13.34, 15.19, 22.82, 29.87, 29.95, 34.11, 43.98, 48.69.

Example 26

N-ethyl-N[(3-propylsulfinyl)-propyl]amine

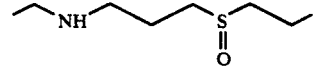

A solution ethyl-(3-propylthio)-propylamine (1.61 g, 10 mmOl) was oxidized with 3-chloroperbenzoic acid (2.1 g, 10 mmol) in analogy with example 2. The title compound recrystallized as hydrochloride from ethyl acetate. Yield: 1.7 g.

NMR: $^{13}$C in CDCL$_3$; 12.77, 14.68, 15.65, 22.68, 43.28, 47.77, 49.75, 53.84

Example 27

4-[3-[ethyl[3-(propylsulfinyl)propyl]amino]-2-hydroxypropoxy]-benzonitrile

A solution of 4-(oxiranylmetoxy)-benzonitrile (0.2 g, 1.13 mmol) and ethyl-(3-propylsulfinyl)-propylamine (0.2 g, 1.13 mmol) in acetonitrile (8 ml) was refluxed over night. The solvent was evaporated and the residue was dissolved in hydrochloric acid, washing with ether followed by alkalizing with sodium hydroxide and extracting with methylene chloride yielded 0.33 g of the title compound.

NMR: $^{13}$C in CDCL$_3$; 11.31, 11.43, 13.35, 16.30, 20.46, 20.64, 47.71, 47.76, 49.65, 50.15, 52.38, 52.86, 54.65, 54.78, 56.41 , 56.45, 66.09, 70.53, 70.61, 104.24, 115.29, 119.04, 133.92, 162.00

Example of Pharmaceutical Compositions

The following examples illustrate the preparation of pharmaceutical compositions of the invention. The wording "active substance" denotes a compound according to the present invention or a salt thereof.

Formulation A. Soft Gelatin Capsules 500 g of active substance were mixed with 500 g of corn oil, whereupon the mixture was filled in soft gelatin capsules, each capsule containing 100 mg of the mixture (i.e. 50 mg of active substance).

Formulation B. Soft Gelatin Capsules 500 g of active substance were mixed with 750 g of pea nut oil, whereupon the mixture was filled in soft gelatin capsules, each capsule containing 125 mg of the mixture (i.e. 50 mg of active substance).

Formulation C. Tablets 500 g of active substance were mixed with 200 g of silicic acid of the trademark Aerosil. 450 g of potato starch and 500 g of lactose were mixed therewith and the mixture was moistened with a starch paste prepared from 50 g of potato starch and distilled water, whereupon the mixture was granulated through a sieve. The granulate was dried and sieved, whereupon 20 g of magnesium stearate was mixed into it. Finally the mixture was pressed into tablets each weighing 172 mg.

Formulation D. Effervescing Tablets 100 g of active substance, 140 g of finely divided citric acid, 100 g of finely divided sodium hydrogen carbonate, 3.5 g of magnesium stearate and flavouring agents (q.s.) were mixed and the mixture was pressed into tablets each containing 100 mg of active substance.

Formulation E. Sustained Release Tablet 200 g of active substance were melted together with 50 g of stearic acid and 50 g of carnauba wax. The mixture thus obtained was cooled and ground to a particle size of at most 1 mm in diameter. The mixture thus obtained was mixed with 5 g of magnesium stearate and pressed into tablets each weighing 305 mg. Each tablet thus contains 200 mg of active substance.

| Formulation F. Injection solution | |
|---|---|
| Active substance | 3.0 mg |
| Sodium pyrosulfite | 0.5 mg |
| Disodium edetate | 0.1 mg |
| Sodium chloride | 8.5 mg |
| Sterile water for injection ad | 1.0 ml |

Formulation G. Hard Gelatine Capsules 10 g of active substance was mixed with 400 g of lactose and finally 2 g of magnesium stearate was added. The mixture was then filled in hard gelatine capsules, each capsule containing 206 mg of the mixture (i.e. 5 mg of active substance).

Formulation H. Tablets 50 g of active substance was mixed with 1500 g of lactose, 200 g of microcrystalline cellulose and 10 g magnesium stearate. Tablets of 5 mg active substance with a core weight of 176 mg were finally compressed.

Pharmacology

Drugs which cause a delay of the repolarization process, thereby prolonging the period during which the heart is unable to respond to a new stimulus (the so called effective refractory period), are said to exert a Class III antiarrhythmic action (Vaughan Williams, 1970, 1984). This effect can be recorded as a prolongation of the action potential of myocardial cells, and can be measured directly in transmembrane potential recordings or indirectly in the monophasic action potential. The compounds belonging to this invention have been studied with the latter technique.

Male guinea-pigs are anaesthetized with barbiturate and ventilated with room air under blood gas control. The heart is exposed by thoracotomy and the vagal nerves are cut. A standard electrocardiogram is recorded from skin electrodes, and a monophasic action potential (MAP) is recorded from the epicardial surface of the ventricles, usually from the left one, by a specially designed bipolar electrode, which is gently pressed against the epicardial surface or attached by use of suction pressure. A local electrocardiogram from the area of the MAP electrode is also obtained (between the peripheral electrode and reference from the skin electrodes). Arterial blood pressure is recorded via an arterial cathether in one femoral artery, and intravenous lines are used for infusion of barbiturate and test substance. Since the duration of the depolarization of the heart cells (the MAP duration) is dependent on the frequency, the evaluation of a drug effect must be made at a constant frequency. For that purpose a pacing electrode is attached to the left atrium, and the heart can be electrically stimulated at a constant frequency slightly above the normal sinus node frequency.

The monophasic action potential duration at 75% repolarization is used for primary screening. All experiments are done under $\beta$-adrenoceptor blockade, achieved by pretreatment with 0.5 mg/kg propranolol.

The test substances are administered intravenously during 30 seconds in increasing doses at exact, predeterminated intervals and recordings are made at exact intervals after dosing, both on a Mingograph recorder and on tape for later analysis of the signals by a customdesigned computer program. Dose-response curves are constructed for the different variables, and the doses needed to obtain 10 and 20 per cent prolongation of the MAP duration are derived by interpolation. The dose giving 20 per cent increase of the MAP duration ($D_{20}$ MAP) is used as a measure of potency.

Selected compounds are subject to further testing in anaesthetized and chronically instrumented conscious dogs, in which effects on atrial and ventricular refractoriness are also recorded.

TABLE 1

| Substance according to Example no | $D_{20}$MAP | VERP |
|---|---|---|
| Ex. 1 | 6.7 | n.t. |
| Ex. 2 | 7.3 | + |
| Ex. 3 | 6.8 | n.t. |

$D_{20}$-MAP = -log dose (moles/kg) giving 20 percent increase of the MAP duration in anaesthetized guinea-pigs (see screening method).
Change in ventricular refractoriness (VERP) in anaesthetized and conscious dogs at dose levels equivalent to $D_{20}$-MAP in guinea-pigs.
+ = prolonged VERP
n.t. = not tested

BEST MODE OF CARRYING OUT THE INVENTION

The compound 4-[3-[ethyl[3-(propylsulfinyl)-propyl]amino]-a2-hydroxypropoxy]benzonitrile and their salts, processes for preparing said compound and method employing said compound in therapy represent the best mode of carrying out the invention known to the inventors at present.

We claim:
1. A compound of the formula

$$\underset{CN}{\underset{|}{C_6H_4}}-O-(CH_2)_n-Y-\underset{\underset{A}{|}}{\overset{Z}{\overset{|}{C}}}$$

and when appropriate in the form of a racemic mixture or in the form of a steroisomeric component or the pharmaceutically acceptable salts thereof, in which formula
n is 1,
Y is $CH_2$, CHOH, or CHF,
Z is hydrogen,
A is a group $$-N(R_a)-(CH_2)_s-\overset{(O)_p}{\overset{\|}{S}}-R_c$$

wherein $R_a$ is a straight or branched hydroxy alkyl or an alkyl group containing 2–5 carbon atoms and optionally substituted by one or more fluoro atoms,
$R_c$ is a saturated or unsaturated, straight or branched alkyl group containing 1–4 carbon atoms and optionally substituted by one or more fluoro atoms,
p is 1 or 2,
s is 3 or 4

2. A compound according to claim 1 wherein $R_a$ is $C_2H_5$, $C_3H_7$, $CH_2CH_2OH$, $CH_2CHOHCH_3$,
$R_c$ is $C_2H_5$, $C_3H_7$, $CH_2CHFCH_3$,
s is 3 or 4.

3. A compound according to claim 2 wherein p is 1.
4. A compound according to claim 3 wherein Y is CHOH, $CH_2$,
$R_a$ is $C_2H_5$, $CH_2CH_2OH$,
s is 3,
$R_c$ is $C_3H_7$.

5. A compound of the formula $$\underset{CN}{\underset{|}{C_6H_4}}-O-CH_2-\underset{\underset{OH}{|}}{CH}-CH_2-\underset{\underset{C_2H_5}{|}}{N}-(CH_2)_s-\overset{O}{\overset{\|}{C}}-R_c$$

wherein s is 3 or 4,
$R_c$ is $C_2H_5$, $C_3H_7$, $CH_2CHFCH_3$,
a racemic mixture thereof, a stereoisomer thereof, or a pharmaceutically acceptable salt thereof.

6. 4-[3-[ethyl[-3-(propylsulfinyl)propyl]amino]-2-hydroxypropoxy]bensonitrile or a pharmaceutically acceptable salt thereof.

7. 4-[3-[ethyl[-3-(propylsulfinyl)propyl]amino]-2(R)-hydroxypropoxy]benzonitrile or a pharmaceutically acceptable salt thereof.

8. 4-[3-[ethyl[-3-(propylsulfinyl)propyl]amino]-2(S)-hydroxypropoxy]benzonitrile or a pharmaceutically acceptable salt thereof.

9. 4-[3-[ethyl[-4-(ethylsulfinyl)butyl]amino]2-hydroxypropoxy]benzonitrile or a pharmaceutically acceptable salt thereof.

10. 4-[3-[ethyl[-3-[(2-fluoropropyl)sulfinyl]-propyl]amino]-2-hydroxypropoxy]benzonitrile or a pharmaceutically acceptable salt thereof.

11. A pharmaceutical preparation comprising as active ingredient a therapeutically effective amount of a compound of the formula $$\underset{CN}{\underset{|}{C_6H_4}}-O-CH_2-\underset{\underset{OH}{|}}{CH}-CH_2-\underset{\underset{C_2H_5}{|}}{N}-(CH_2)_s-\overset{O}{\overset{\|}{C}}-R_c$$

wherein s is 3 or 4,
$R_c$ is $C_2H_5$, $C_3H_5$, $CH_2CHFCH_3$,
a racemic mixture thereof, a stereoisomer thereof or a pharmaceutically acceptable salt thereof in association with a pharmaceutically accepted carrier.

12. A pharmaceutical preparation comprising as active ingredient a therapeutically effective amount of 4-[3-[ethyl[-3-(propylsulfinyl)propyl]amino]-2-hydroxypropoxy]benzonitrile or a pharmaceutically acceptable salt thereof in association with a pharmaceutically acceptable carrier.

13. A pharmaceutical preparation comprising as active ingredient a therapeutically effective amount of 4-[3-[ethyl[-3-(propylsulfinyl)propyl]amino]-2(R)-hydroxypropoxy]benzonitrile or a pharmaceutically acceptable salt thereof in association with a pharmaceutically acceptable carrier.

14. A pharmaceutical preparation comprising as active ingredient a therapeutically effective amount of 4-[3-[ethyl[-3-(propylsulfinyl)propyl]amino]-b 2-(S)-hydroxypropoxy]benzonitrile or a pharmaceutically acceptable salt thereof in association with a pharmaceutically acceptable carrier.

15. A pharmaceutical preparation comprising as active ingredient a therapeutically effective amount of 4-[3-[ethyl[-4-(ethylsulfinyl)butyl]amino]-2-hydroxypropoxy]benzonitrile or a pharmaceutically acceptable salt thereof in association with a pharmaceutically acceptable carrier.

16. A pharmaceutical preparation comprising as active ingredient a therapeutically effective amount of 4-[3-[ethyl[-3-[(2-fluoropropyl)sulfinyl]propyl]amino]-2-hydroxypropoxy]benzonitrile or a pharmaceutically acceptable salt thereof in association with a pharmaceutically acceptable carrier.

17. A method for the treatment of cardiac arrhythmia in mammals, comprising the administration to a mammal in need of such treatment of an effective amount of a compound.

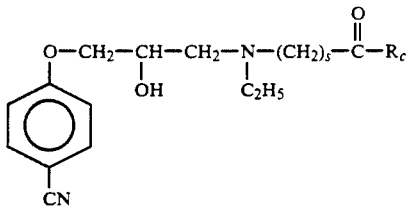

wherein s is 3 or 4, $R_c$ is $C_2H_5$, $C_3H_7$, $CH_2CHFCH_3$, a racemic mixture thereof, a stereoisomer thereof or a pharmaceutically acceptable salt thereof.

18. A method as in claim 17 wherein the compound is 4-[3-[ethyl[-3-(propylsulfinyl)propyl]amino]-2-hydroxypropoxy]benzonitrile.

19. A method as in claim 17 wherein the compound is 4-[3-[ethyl[-3-(propylsulfinyl)propyl]amino]-2(R)-hydroxypropoxy]benzonitrile.

20. A method as in claim 17 wherein the compound is 4-[3-[ethyl[-3-(propylsulfinyl)propyl]amino]-b 2-(S)-hydroxypropoxy]benzonitrile.

21. A method as in claim 17 wherein the compound is 4-[3-[ethyl[-4-(ethylsulfinyl)butyl]amino]-2-hydroxypropoxy]benzonitrile.

22. A method as in claim 17 wherein the compound is 4-[3-[ethyl[-3-[(2-fluoropropyl)sulfinyl]propyl]amino]-2-hydroxypropoxy]benzonitrile.

* * * * *

UNITED STATES PATENT AND TRADEMARK OFFICE
CERTIFICATE OF CORRECTION

PATENT NO. : 5,155,133

DATED : October 13, 1992

INVENTOR(S) : Almgren et al.

It is certified that error appears in the above-identified patent and that said Letters Patent is hereby corrected as shown below:

Title page, item [57], line 35, in the second instance,
$$"\begin{array}{c}(O)_p\\|\\-S-R_c\end{array}"\ \text{should read}\ --\begin{array}{c}(O)_p\\||\\-S-R_c\end{array}--;$$

col. 2, lines 27-29, in the second instance,
$$"\begin{array}{c}(O)_p\\|\\-S-R_c\end{array}"\ \text{should read}\ --\begin{array}{c}(O)_p\\||\\-S-R_c\end{array}--;$$

col. 2 , line 38, the second "Ra''" should read --Ra-- and the third "Ra''" should read --Ra'--;

col. 3, line 1, "instance" should be in the normal font;

col. 3, line 46, after "propyl]" delete "-";

col. 4, line 11, after "4-" insert -- [ --;

col. 4, line 19, there are too many spaces between "thio propyl;

col. 4, line 32, there are too many spaces between "3-(4-";

col. 4, line 33, "propy" should read --propyl--;

col 5, line 4&5, "Particularly preferred compounds are" should be on line 5;

UNITED STATES PATENT AND TRADEMARK OFFICE
CERTIFICATE OF CORRECTION

PATENT NO. : 5,155,133

DATED : October 13, 1992

INVENTOR(S) : Almgren et al.

It is certified that error appears in the above-identified patent and that said Letters Patent is hereby corrected as shown below:

col. 7, line 49, "The" should not be indented and "carries" should read --carried--;

col. 10, line 63, "4[-" should read -- 4-[ --;

col. 11, line 43, after "3-[ethyl[" delete "b"

col. 11, line 63-64, delete both lines because they duplicated lines 66-67;

col. 12, line 14, after "7.3 g of 4-" insert --[--;

col. 17, line 26, "propy]" should read --propyl]--;

col. 17, line 66, after "propoxy]" delete "-";

col. 18, line 13, "amin" should read --amino--;

col. 18, line 30, after "propoxy]" delete "-";

col. 19, line 15, "c)" should be on line 16 in front of "4-[3";

col. 19, line 18, after "4-[3" delete "{" and insert -- -( --;

col. 19, line 25, "$CH_{3tOH(}9:1)$" should read --$CH_3OH(9:1)$--;

col. 19, line 67, after "hydroxypropoxy]" insert -- - --;

UNITED STATES PATENT AND TRADEMARK OFFICE
CERTIFICATE OF CORRECTION

PATENT NO. : 5,155,133

DATED : October 13, 1992

INVENTOR(S) : Almgren et al.

It is certified that error appears in the above-identified patent and that said Letters Patent is hereby corrected as shown below:

col. 20, line 55, after "3-[ethyl" insert --3--.

col. 22, line 54, after "(133" insert --g, 1 mol) was added--;

col. 25, line 28, after "]amino]-" delete "a";

col. 26, line 13,
"$-(CH_2)_s-\overset{O}{\overset{\|}{C}}-R_c$" should read --$-(CH_2)_s-\overset{O}{\overset{\|}{S}}-R_c$--;

col. 26, line 34, after "butyl]amino]" insert -- - --;

col. 26, line 37, after "4-[3-[ethyl[" delete "-";

col. 26, line 46,
"$-(CH_2)_s-\overset{O}{\overset{\|}{C}}-R_c$" should read --$-(CH_2)_s-\overset{O}{\overset{\|}{S}}-R_c$--;

col. 26, line 55, "$C_3H_5$" should read --$C_3H_7$-- col. 26, line 61, after "4-[3-[ethyl[" delete "-";

col. 26, line 67, after "4-[3-[ethyl[" delete "-";

col. 27, line 6, after "4-[3-[ethyl[" delete "-";

UNITED STATES PATENT AND TRADEMARK OFFICE
CERTIFICATE OF CORRECTION

PATENT NO. : 5,155,133
DATED : October 13, 1992
INVENTOR(S) : Almgren et al.

It is certified that error appears in the above-identified patent and that said Letters Patent is hereby corrected as shown below:

col. 27, line 6, after "amino]-" delete "b" and there are too many spaces between "amino]-" and "2-(S)-";

col. 27, line 13, after "4-[3-[ethyl[" delete "-";

col. 27, line 21, after "4-[3-[ethyl[" delete "-";

col. 28, line 4,
"        O      " should read --        O    --;
        ||                              ||
-(CH$_2$)$_s$-C-R$_c$                  -(CH$_2$)$_s$-S-R$_c$ col. 28, line 16, after "4-[3-[ethyl[" delete "-";

col. 28, line 19, after "4-[3-[ethyl[" delete "-";

col. 28, line 22, after "4-[3-[ethyl[" delete "-";

col. 28, line 22, after "amino]-" delete "b" and there are too many spaces between "amino]-" and "2-(S)-";

col. 28, line 25, after "4-[3-[ethyl[" delete "-";

col. 28, line 28, after "4-[3-[ethyl[" delete "-";

Signed and Sealed this

Fifteenth Day of November, 1994

Attest:

BRUCE LEHMAN

Attesting Officer

Commissioner of Patents and Trademarks